United States Patent [19]

Russo

[11] 4,202,098
[45] May 13, 1980

[54] DENTAL PLATE CUSHION

[76] Inventor: Leonard Russo, 177 Canal St., San Rafael, Calif. 94901

[21] Appl. No.: 11,256

[22] Filed: Feb. 12, 1979

[51] Int. Cl.$^2$ ............................................. A61C 13/00
[52] U.S. Cl. .................................................. 433/168
[58] Field of Search ............................................. 32/2

[56] References Cited

U.S. PATENT DOCUMENTS

| 2,664,631 | 1/1954 | Hollander et al. | 32/2 |
| 3,226,826 | 1/1966 | Town | 32/2 |

*Primary Examiner*—Robert Peshock

[57] ABSTRACT

A method of cushioning and retaining a dental plate that eliminates the need for adhesives and provides the wearer a choice of thicknesses that is for all practical purposes continuous. A denture cushion according to the present invention comprises one or more sheets of cellulose filter material. The sheet periphery is shaped to cover the gum and palate confronting portions of the plate, and fits in the region between the plate and the wearer's mouth. A cushion for the lower plate has a U-shaped configuration while a cushion for the upper plate has a generally rounded or oval configuration, preferably with a plurality of peripheral notches to make the cushion more easily conform to the contour of the wearer's palate. In use, the wearer places a number of such sheets in a stack to make a cushion of the appropriate thickness and moistens them. The moistened stack is then placed on the dental plate for placement in the mount, after which the wearer's saliva cooperates with the sheet material to keep the denture in place. Despite the absence of adhesive, a surprising degree of adhesion results, thus providing the user with a high degree of comfort and mental security. The cushion does not disintegrate in use, and may be easily removed when the denture is removed. Due to the inert nature of the material employed, food flavors are left substantially unchanged.

11 Claims, 4 Drawing Figures

U.S. Patent  May 13, 1980  4,202,098
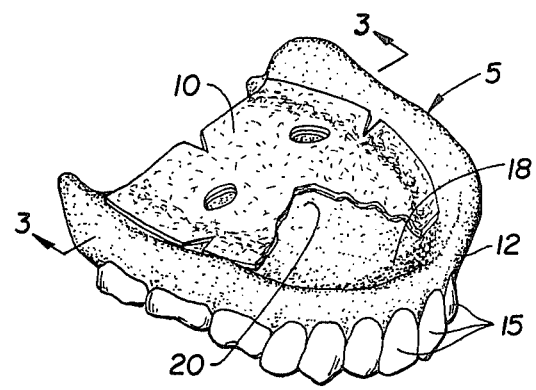
Fig.—1.
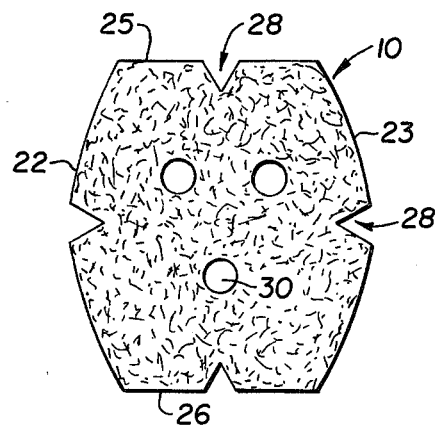
Fig.—2.
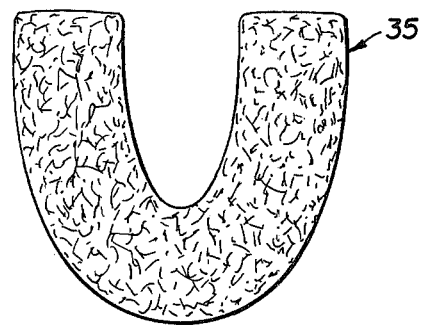
Fig.—4.
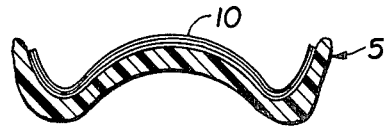
Fig.—3.

DENTAL PLATE CUSHION

BACKGROUND OF THE INVENTION

Broadly, a dental plate (denture) is a prosthetic device that provides a user with artifical teeth to replace missing ones. A full dental plate is required when the wearer has lost all of his upper or lower teeth, and comprises a relatively hard plastic or rubber body that conforms to the contours of the wearer's upper of lower gums, and a plurality of artificial teeth mounted thereto. Typically, the denture is cast from a mold that is taken from the wearer's mouth in order that it conforms as closely as possible to the actual contours of the wearer's mouth. Despite advances in techniques and materials for making the molds and the dental plate itself, variations inevitably occur, in part due to normal changes in the wearer's mouth. Thus after time the denture typically bears on localized portions of the gum and palate tissues, thereby causing discomfort to the wearer. In the extreme, ill-fitting dentures may cause permanent damage to the bone structure of the mouth.

A further problem with ill-fitting dentures is that when the wearer attempts to chew or bite various kinds of foods, the denture comes loose to the embarrassment of the wearer. This problem is most severe with the upper dental plate due to gravity. Often, in an effort to minimize discomfort and/or embarrassment, the wearer avoids thoroughly chewing his food, thereby increasing the risk of digestive problems and the like.

In recognition of these problems, many devices and preparations have been developed to provide an adhesive cushion between the hard denture material and the relatively soft mouth tissue to maintain the denture in position despite the forces that arise when the wearer chews anything but the softest food. One preferred solution to the problem is to lay a bead of water insoluble, viscous adhesive compound along the gum confronting portion of the denture so that when the denture is pressed into place, the bead of material flows outwardly over the gum tissue to provide a suction seal and cushioning effect. Since such material is relatively insoluble in water, it presents cleanup problems that tend to render its use undesirable. For example, in addition to having to remove the material that adheres to the dental plate when it is removed from the mouth, the user must also scrape away a portion of the adhesive material that remains on his gums. Depending on the amount of material to be removed and any possible soreness of the gums, this can be a most unpleasant and/or embarrassing task. Granular adhesives adapted to be sprinkled on a wetted denture are less messy to clean up, but have the disadvantage that the material sloughs off and is swallowed within a few hours, thereby making it necessary for the wearer to move his dentures and reapply the material. Given the wide variety of situations in which denture wearers find themselves, it is clear that under certain circumstances this is impossible, so that the user then finds himself without either the cushioning or adhesive benefits of the preparation. Both the viscous and granular adhesive materials may also affect the taste of food.

A different approach to the problem employs an impregnated fabric pad. Such a pad may be impregnated with an adhesive material while still largely avoiding the problem of adhesive residue since the bulk of the adhesive comes off within the fabric matrix. Alternately, the pad may be impregnated with a water insoluble wax-like material which does not become adhesive in use, but which softens to make the pad conform to the desired configuration and retain such a configuration. Along this line, a preformed cotton fiber pad may be used.

One feature that the above described denture pads have in common is that they are relatively costly, such cost being in part necessitated by the various processing steps in their fabrication. Thus financially poor users are sometimes tempted to wash and reuse the pads, even where the manufacture has specified that a fresh pad is to be used each day. Such reuse is unsound from a hygienic point of view, and further reduces the efficacy of the product. The seriousness of this problem is compounded since the poorer denture wearers are the ones who are most likely to be troubled by ill-fitting dentures. Moreover, hygiene facilities may be poorer for those very wearers who are most tempted to reuse the pads. A further difficulty with the various pad materials is that they are generally available in a small number of thicknesses. This may present a problem to a denture wearer who requires a pad having a thickness that is between two available thicknesses. Moreover, in the event that a user is experiencing a certain amount of swelling, different thicknesses may be needed from one day to the next.

SUMMARY OF THE INVENTION

The present invention provides a method of cushioning and retaining a dental plate that eliminates the need for adhesives and provides the wearer a choice of thicknesses that is for all practical purposes continuous. The material used to practice the method is sufficiently inexpensive that even a poor user can readily afford fresh material each day so that hygienic problems are avoided.

Broadly, a denture cushion according to the present invention comprises one or more sheets of cellulose filter material. The sheet periphery is shaped to cover the gum and palate confronting portions of the plate, and the sheet is maintained in the region between the denture and the wearer's mouth. Accordingly, a cushion for the lower plate has a U-shaped configuration while a cushion for the upper plate has a generally rounded or oval configuration, possibly trunicated preferably with a plurality of peripheral notches to make the cushion more easily conform to the contour of the wearer's palate. The upper plate cushion may also be provided with one or more apertures in its central portion to relieve excess moisture.

In use, the wearer places a number of such sheets in a stack to make a cushion of the appropriate thickness and moistens them. The moistened stack is then placed on the dental plate for placement in the mouth, after which the wearer's saliva cooperates with the sheet material to keep the denture in place. Despite the absence of adhesive, a surprising degree of adhesion results, thus providing the user with a high degree of comfort and mental security. The cellulose filter material, as is appropriate for its originally intended use, has a high degree of wet strength and contains virtually no water-soluble components in its makeup. Thus the cushion does not disintegrate in use, and may be easily removed when the denture is removed. At the same time, a cushion according to the present invention may be left in position on the plate when the plate is periodically removed and rinsed. Due to the absence of a foreign compound within the mouth, when the present invention is employed, food flavors are left substantially unchanged.

For a further understanding of the nature and advantages of the present invention, reference should be had to the remainder of the specification and the attached drawings.

BRIEF DESCRIPTION OF THE DRAWINGS

FIG. 1 is a perspective view of an upper dental plate showing a dental plate cushion according to the present invention positioned thereon;

FIG. 2 is a plan view of an upper dental plate cushion according to the present invention;

FIG. 3 is a sectional view taken along line 3—3 of FIG. 1; and

FIG. 4 is a plan view of a lower dental plate cushion according to the present invention.

DETAILED DESCRIPTION OF THE DRAWINGS

FIG. 1 is a perspective view of an upper dental plate 5, on which is positioned a dental plate cushion 10, shown partially cut away. As can be seen, upper dental plate 5 comprises a tooth supporting body 12 and a plurality of artificial teeth 15 mounted thereto in a manner simulating the disposition of upper teeth in a human mouth. Tooth supporting body 12 has an upper surface characterized by a U-shaped concavity 18 adapted to confront the upper gums of the denture wearer and a central convex portion 20 that confronts the wearer's palate.

FIG. 2 is a plan view of cushion 10. Cushion 10 is generally oval, but has its ends truncated, thus defining opposed curved side edges 22 and 23 and opposed straight front edge 25 and straight rear edge 26. Each of edges 22, 23, 25 and 26 is preferably notched at a central location with a V-shaped notch 28 to aid in the cushion's conforming to the contour of the wearer's palate. Upper plate cushion 10 may also be provided with central apertures 30 which relieve excess moisture and permit saliva to flow out, thereby improving somewhat the suction between plate 5 and the wearer's mouth.

Dental plate cushion 10 is preferably constructed from one or more sheets of commercially available cellulose filter material that are cut into the shape described above. The thickness of one layer of such material is in the neighborhood of 0.002 inches (0.05 mm). Six sheets of filter material are typical. In use, the wearer takes a number of sheets required to form a cushion of the desired thickness, moistens them slightly, and places the moistened stack on the mouth confronting portion of the dental plate prior to insertion into the mouth. The placement can be best seen with reference to FIGS. 1 and 3. It can be seen that the relative thinness of the cellulose filter material allows the wearer to form a cushion of almost continuously variable thickness with increments of approximately 0.002 inches (0.05 mm) possible. Although the sheets will usually all be similarly configured, it may sometimes be desirable to trim some of the sheets to a smaller size or to remove interior portions of some sheets to provide a cushion non-uniform thickness.

The shape of cushion 10 with its opposed straight edges 25 and 26 provides for convenient stacking of the sheets. In particular, a long strip of the filter material may be folded in accordian fashion at intervals equal to the distance between edges 25 and 26 to form a relatively large stack. The curved side edges may than be cut to the desired configuration. The wearer may then form the cushion defining stack of desired thickness by making one tear along one fold which joins two adjacent sheets. Since each sheet in the stack is joined along an edge to each contacting sheet, all the sheets are maintained in precise registration.

Once dental plate 5 and cushion 10 are in the mouth, the wearer's saliva acts with the dental plate cushion to provide a suction seal and further relieves any localized pressures that might be present. It is important to note that no additional adhesive material is used with the cellulose filter sheet material, and despite the absence of such adhesive, the plate is maintained in position with a surprising degree of effectiveness. Thus, the wearer is able to eat and talk substantially normally without the fear and embarrassment that typically accompany loose or potentially loose dentures. When the dental plate denture is removed periodically during the day for rinsing, the cushion is easily removed with it and may be rinsed and replaced with the plate. At the same time, the filter material is sufficiently inexpensive that daily replacement of the cushion does not represent a significant expense.

While lower dental plates do not pose as severe a problem as upper ones, the present invention is also applicable to lower plates. In particular, FIG. 4 shows in plan view a lower dental plate cushion 35 which is of a generally U-shaped configuration adapted to fit along a gum confronting portion of a lower dental plate, not illustrated.

The properties of cellulose filter material are ideally suited to use as a dental plate cushion since the material does not disintegrate when it gets wet. Furthermore, due to the inert nature of such filter material, the denture wearer does not experience the sensation of a foreign substance in his mouth, and the cushion imparts no foreign flavors to food that is eaten.

Thus, it can be seen that the present invention provides a suprisingly inexpensive and effective method of cushioning and retaining dentures without adhesive and wherein the thickness of the cushion may be chosen substantially at will. While the above provides a full and complete disclosure of the preferred embodiment of the invention, various modifications, alternate constructions, and equivalents may be employed without departing from the true spirit and scope of the invention. For example, the shape of the upper plate cushion need not have straight edges along the front and rear, but may be otherwise contoured. Therefore, the above description and illustrations should not be construed as limiting the scope of the invention which is defined by the appended claims.

What is claimed is:

1. A denture cushion consisting essentially of moistened cellulose filter sheet material, inserted onto a mouth confronting portion of the denture, whereby when the wearer inserts the denture, with filter sheet material so placed, in his mouth and bites down to seat the dentures on his gums, the cellulose compresses and through suction causes the denture to adhere in its seated position on said gums and eliminates the need for conventional denture adhesives.

2. The invention of claim 1 wherein said denture is an upper dental plate and wherein said sheet material has a generally oval configuration with a plurality of notches at the periphery to facilitate fitting between said denture and the palate of said wearer.

3. The invention of claim 2 wherein said oval is truncated at its ends to define opposed straight edges.

4. The invention of claim 1 wherein said denture is a lower dental plate and wherein said sheet material is of a U-shaped configuration adapted to fit between said denture and the lower gums of said wearer.

5. A method of increasing the adhesion and conformity of a denture to a user's mouth comprising the steps of:
placing a layer consisting essentially of cellulose filter sheet material onto a mouth confronting portion of the denture;
moistening the layer of cellulose filter sheet material; and
seating the denture and layer of cellulose filter sheet material so placed on the wearer's gums so that the cellulose compresses and through suction causes the denture to adhere in its seated position on said gums and eliminates the need for conventional denture adhesives.

6. The invention of claim 5 wherein said step of moistening the layer of cellulose filter sheet material is carried out before said step of seating the denture.

7. The invention of claim 5 wherein said step of placing the layer is carried out on substantially the entire mouth confronting portion of the denture.

8. A denture cushion for use with a denture in the mouth of a wearer consisting essentially of moistened cellulose filter material in the form of a plurality of sheets, insertable onto a mouth confronting portion of said denture with a peripheral edge of at least one of said sheets generally commensurate with said mouth confronting region of said denture.

9. The invention of claim 8 wherein all of said sheets are of substantially equal size.

10. The invention of claim 8 wherein a first of said plurality of sheets is joined to a second of said plurality of sheets along a common folded edge.

11. The combination of a denture having a mouth tissue confronting region and a moistened layer consisting essentially of cellulose filter sheet material placed on at least a portion of said mouth tissue confronting region such that when said combination is seated on a wearer's gums adhesion of said denture within the mouth of the wearer is improved and localized pressures exerted by said denture on the mouth tissue of the wearer are eased without the use of adhesive material.

* * * * *